United States Patent [19]
de la Guardia et al.

[11] 4,303,085
[45] Dec. 1, 1981

[54] SYSTEM AND METHOD FOR HAIR TREATMENT

[75] Inventors: Mario de la Guardia, Savannah, Ga.; Donald R. Cowsar, Birmingham, Ala.

[73] Assignee: Carson Products Company, Savannah, Ga.

[21] Appl. No.: 120,091

[22] Filed: Feb. 11, 1980

Related U.S. Application Data

[63] Continuation-in-part of Ser. No. 805,149, Jun. 9, 1977.

[51] Int. Cl.$^3$ .............................................. A45D 7/00
[52] U.S. Cl. ...................................................... 132/7
[58] Field of Search ....................... 132/7; 424/71, 79; 210/24

[56] References Cited

U.S. PATENT DOCUMENTS 2,781,290  2/1957  Martin ................................... 424/79
2,838,440  6/1958  Thurmon ........................... 424/79 X
2,857,311  10/1958  Thurmon .............................. 424/79
3,154,470  10/1964  Braun ..................................... 424/89

Primary Examiner—G. E. McNeill
Attorney, Agent, or Firm—Newton, Hopkins & Ormsby

[57] ABSTRACT

Systems and methods for curling hair and for straightening hair are disclosed, wherein the systems contain, as a principal active ingredients thereof, guanidine hydroxide, together with an ion exchange resin. The guanidine hydroxide is prepared by mixing together in an aqueous medium at least one water-soluble guanidine salt and at least one particulate, strong-base, quaternary ammonium, hydroxide-form ion-exchange resin. After the mixed components have had a chance to undergo ion exchange, the composition is applied to hair which is maintained in a desired configuration, and after the composition has been in contact with the hair for an effective time the composition is removed from the hair, thereby causing the hair to maintain such desired configuration.

15 Claims, No Drawings

SYSTEM AND METHOD FOR HAIR TREATMENT

CROSS REFERENCE TO RELATED APPLICATIONS

This application is a continuation-in-part of co-pending application Ser. No. 805,149 filed by Mario de la Guardia on June 9, 1977.

BACKGROUND OF THE INVENTION

Commercial products based upon compositions containing thioglycolates, sulfites or alkali metal hydroxides, such as sodium hydroxides, have been widely used to permanently straighten unstraight hair, especially to straighten unstraight Negro hair. Of these products, the thioglycolate compositions and the sulfite compositions which have been commercially marketed have been relatively ineffective, with the hair in many cases reverting at least partially to the original unstraight form. While very effective in producing the desired straightening effect, sodium hydroxide compositions are very harsh to both the scalp and the hair, and the use of such compositions has resulted in numerous instances of scalp irritation and/or burning, and has also resulted in a substantial reduction of the strength of the treated hair, and even, in some instances, considerable hair loss.

Various guanidine compounds have been evaluated by the prior art in hair waving or hair straightening compositions. Of these guanidine thioglycolate appears to have had the most attention by researchers in this art. See, for example, Shansky, *American Perfumer and Cosmetics*, Volume 78, August, 1963, 32–34; Bogaty et al, *American Perfumer and Cosmetics*, Volume 78, November, 1963, pages 45–47; and Shansky, *American Perfumer and Cosmetics*, Volume 78, December, 1963, pages 29–30.

Various organic bases including guanidine have been found to accelerate the dehairing effect of calcium hydroxide suspensions. See, e.g. Barry, "Delipatories" *Cosmetic Science and Technology*, Edited by Balsam and Sagarin, 2nd Edition, Volume 2, Chapter 18, page 39, 45, Wiley Interscience, New York, 1972 and Barry "Depilatories" *Cosmetic Science and Technology*, Edited by Sagarin, First Edition, Chapter 20, page 461–462, Interscience Publishers, New York, 1957, and references cited therein.

The co-pending application of Mario de la Guardia, Ser. No. 805,149, filed June 9, 1977, discloses that guanidine hydroxide is an effective human hair straightening or relaxing composition, as well as an effective permanent wave composition. The compositions exhibit improved hair strength retention and significantly reduce scalp irritation, compared to hair relaxing compositions based on alkali metal hydroxides. The permanent relaxation effect is generally as good as that achieved by the use of alkali metal hydroxides (such as sodium hydroxide).

U.S. Pat. No. 3,157,578, Nov. 17, 1964, discloses compositions for the permanent waving of human hair utilizing a solution containing, e.g. thioglycollic acid and guanidine carbonate. These compositions are employed in the form of aqueous solutions having a pH value of from 7–9, with the guanidine used to replace ammonia used previously thereto, both to function as a neutralizing agent for the acid reducing agent, and also in the form of ammonium carbonate for pH control.

U.S. Pat. No. 3,861,868 of Jan. 21, 1975 acknowledges, in column 1 thereof, earlier abandoned applications relating to the use of guanidine salts in hair dying compositions and hair bleaching compositions.

British Pat. No. 1,274,565 of May 17, 1972 discloses a process for the straightening of human hair wherein the hair straightening is conducted in two separate stages. In the first stage, a known keratin softening substance, such as an alkali hydroxide, sulfite or bisulfite, or a salt of a mercaptocarboxylic acid, is permitted to act upon the hair. After the extensive removal of the keratin softening component, a media containing a swelling substance is applied to the hair. Suitable swelling agents include monovalent aliphatic alcohol, aromatic alcohols, aliphatic diols, ether alcohols, sulfoxides, sulfones, thiocyanates, thiourea and urea, and water-soluble derivatives thereof.

U.S. Pat. No. 3,865,930 of Feb. 11, 1975 discloses a permanent wave composition based on a two-stage operation, wherein in the first stage the S-S linkages of the keratin fiber are opened at an alkaline pH with the addition of a reducing agent such as a thiol. The hair is then treated in a second stage with an oxidizing or neutralizing agent to reconstitute the S-S bridges, so as to impart to the hair the desired configuration. The patent relates to a composition for the aforesaid second stage, wherein the S-S bridges are reformed. This composition is a two-component composition, with one component based on a water-soluble sulfite, bisulfite, metabisulfite or thiourea, and the other component is hydrogen peroxide.

U.S. Pat. Nos. 2,817,342 of Dec. 24, 1957 and 2,840,086 of June 24, 1958 relate to permanent waving compositions based upon sulfite-type materials. Among other acid sulfites disclosed are an acid solution of guanidine bisulfite, formed by bubbling sulfur dioxide gas into an aqueous solution of guanidine carbonate.

Japanese patent 76-9013 discloses hair waving or straightening treatments wherein the hair is initially treated with a weak alkali, followed by a treatment with a chelating metallic salt solution. Calcium oxide or calcium hydroxide is used as a chelating agent to prevent mutual interactions of the active ingredients.

U.S. Pat. No. 2,836,543 of May 27, 1954 discloses the use of guanidine as a swelling agent component in a hair setting composition. The composition also includes a water-soluble sulfite and a polyfunctional aromatic additive compound, such as genetistic acid, which acts as an accelerator.

U.S. Pat. No. 3,642,429 of Feb. 15, 1972 is directed to a hair treatment composition based on a polycondensate of methylol compounds and an urein compound. The generic formula for the urein compound appears to encompass guanidine, but guanidine is not named in that patent.

U.S. Pat. No. 3,686,296 is directed to depilatories which are nitrogen-based thioglycerol molecular complexes. The nitrogen base may be, e.g. guanidine or guanidine hydrochloride.

SUMMARY OF THE INVENTION

The present invention is based on the discovery that effective human hair straightening or relaxing compositions, or human hair permanent wave compositions, based on guanidine hydroxide can be prepared by mixing together in an aqueous medium at least one water-soluble guanidine salt and at least one particulate, strongbase, quaternary ammonium, hydroxide-form ion-exchange resin. The resin should have an affinity for the anion of the guanidine salt which is at least equal to the affinity of the resin for the hydroxyl ion. The composition including the ion-exchange resin is applied to the hair, allowed to maintain contact with the hair for an effective time, and then removed from the hair.

The present invention also includes the system for treating hair to cause the hair to maintain a desired configuration. The system is based upon an aqueous medium which contains a hair treating-effective amount of guanidine hydroxide together with at least one particulate, strong-base, quaternary ammonium ion-exchange resin having bound to the resin at least a stoichiometric amount, based on the amount of the guanidine hydroxide, of an anion which combined with the guanidine ion produces a water-soluble salt. The resin has an affinity for the anion which is at least as great as for the hydroxyl ion.

The system can be applied to hair, and the guanidine hydroxide in the system will cause the desired hair treatment. After the hair has been treated for an effective length of time, the composition remaining on the hair, including the ion-exchange resin, may be readily removed therefrom. For coarser ion-exchange resin, simply combing the hair will remove resin beads and the like. On the other hand, when the ion-exchange resin is finely divided, then a shampooing operation or similar treatment may be required to remove the ion-exchange resin from the hair.

Preferably, the treated hair is fixed or neutralized while the hair is maintained in substantially the desired configuration. Generally the pH value of the hair will be reduced to no greater than about 7 during this step, and preferably the pH of the hair is reduced to about 5.0 to 6.5, although lower pH values may be used if desired. Alternatively, the hair may be neutralized with a neutralizing solution, such as an acidic shampoo. When using such neutralizing solutions, especially shampoos, the curlers or other means of retaining the hair in a desired configuration may be removed from the hair, or these steps may be accomplished while the hair is maintained on curlers or the like as is known to the art. Thereafter, the hair can be conventionally dried, using a blow dryer or the like.

DETAILED DESCRIPTION OF THE INVENTION

Unstraight hair is straightened according to the method of the present invention, by contacting the hair with a straightening amount of the system of the present invention, and straightening the hair during at least a portion of the time that the system is in contact therewith. Furthermore, hair is curled or waved by contacting the hair with a curling amount of the system of the present invention, and curling the hair during at least a portion of the time that the composition is in contact therewith. The system is formed by mixing in an aqueous medium at least one water-soluble guanidine salt and at least one particulate, strong-base, quaternary ammonium, hydroxide-form ion-exchange resin which has an affinity for the anion of the guanidine salt which is at least equal to the affinity of the resin for the hydroxyl ion. The system is applied to the hair, allowed to remain in contact with the hair for an effective length of time, and then removed from the hair.

The ion-exchange resins which are useful in the present invention are strong-base, quaternary ammonium, hydroxide-form ion exchange resins. These resins must be in their hydroxyl form to be useful in the present invention. It is preferred that the resin be one exhibiting maximum basicity and exchange capacity. The resin should have an exchange capacity of at least 2.5 meq/g, preferably at least 3.0 meq/g, more preferably at least 4.0 meq/g. The degree of cross linking in the resin is not critical to the present invention, except to the extent that cross linking may affect other criteria.

Commercially available ion-exchange resins which may be used in the present invention are Duolite A-100 D, A-104 and A-102 D, products of Diamond Shamrock Corporation, Amberlite-IRA-400, -IRA-402, -IRA-420, as well as Amberlite CG-400 type II and type III, products of Rohm and Haas, and Dowex 1×1, 1×2, 1×4, in the 100 to 400 mesh sizes, products of Dow Chemical Company. With most of the above resins, 40 to 50 grams of the resin will be required in order to get conversion of the guanidine salt to guanidine hydroxide. With resins having even higher exchange capacities, however, the amount of resin used can of course be less than indicated above. Normally, however, at least 40 grams of the resin will be utilized. Greater amounts of the resin can be used without adverse effect, from a technical viewpoint, but will add substantially to the cost of the resulting system. The amount of resin used must be at least that amount required to exchange enough anions of the guanidine salt for hydroxyl groups, in order to produce enough guanidine hydroxide to be effective in the treatment of hair, as explained hereinafter.

For resins which are to be removed from the treated hair by shampooing or similar removal methods, it is preferred that the resin be of a mesh size which is less than 200 mesh (U.S. standard screen size), whereas if the resin is to be removed from the hair by combing or the like, then the resin will generally be 40–60 mesh size or larger.

The guanidine salt which is used in the method of the present invention must be water-soluble to an extent that an aqueous solution of the guanidine salt can be prepared having a concentration greater than 0.25 molar in guanidine. A large number of guanidine salts can be utilized, but the salt anion and the particular ion-exchange resin must be chosen such that the affinity of the counter ion for the resin must be equal to or greater than the affinity of the resin for the hydroxide ion, so that a conversion of a substantial amount of the guanidine salt to the hydroxide will be achieved when the aqueous guanidine salt solution is mixed with the hydroxide-form ion-exchange resin. The most preferred guanidine salt is guanidine sulfate, but other guanidine salts which are preferred include the nitrate, the tartrate, the oxylate and the carbonate. Less preferred but operable guanidine salts include the hydrochloride, the sulfite, the phosphate, the fluoride and, as an even less preferred embodiment, the laurate. Guanidine acetate can be utilized, and in general guanidine salts of alkane and alkene carboxylic acids having from 2 to 20 or more carbon atoms can be utilized. The divalent acids are preferred, among the various organic acids. In addition to the salts listed above, guanidine bicarbonate, bisulfite, or bisulfate, as well as guanidine thioglycolate and guanidine alginate, could be used, but are not preferred.

Normally the ion-exchange resin and the guanidine salt will be mixed together at substantially ambient conditions, although elevated or reduced temperatures could be utilized if desired. Normally, however, the reactant temperature will be no lower than 35° F., and no higher than 140° F., as no advantage will be gained by working outside of this range.

After the two components have been admixed together in an aqueous system, the resulting guanidine hydroxide solution should be used within about 48 hours, due to the relative instability of the guanidine hydroxide solution when exposed to ambient conditions. The guanidine hydroxide in the aqueous guanidine hydroxide solution tends to be converted into guanidine carbonate upon exposure to atmospheric carbon dioxide, and the guanidine carbonate is inactive as a hair treating agent according to the method the present invention.

Higher concentrations of guanidine hydroxide in the hair treating composition raise the possibility of greater scalp irritation and more hair damage. The treatment time can generally be reduced with such higher concentrations, so that if adequate care is taken, as may be the case in commercial beauty shop operations, to minimize exposure, such high concentrations may be utilized. In general, the amount of guanidine hydroxide in the relaxer composition can vary from about 1% by weight to about 50% by weight, based on the total weight of guanidine hydroxide plus water and conventional additives, if any, present, but not counting the ion-exchange resin. Concentrations below about 1% by weight are generally too dilute to be effective, and concentrations of guanidine hydroxide in the solution above about 50% by weight generally exceed the solubility limit. It is greatly preferred that the guanidine hydroxide concentration in the solution be within the range of 2 to 20% by weight, based on the total weight of the composition (excluding ion-exchange resin, which is not soluble). More preferably, the guanidine hydroxide concentration is in the range of 3–10% by weight, based on the total weight of the solution, and more preferably the guanidine hydroxide concentration is from 4 to 7% by weight, based on the total weight of the solution.

Enough ion-exchange resin must be used such that the exchange capacity of the amount of resin used is sufficient to convert enough guanidine salt in the solution into guanidine hydroxide, within the above-noted concentration ranges.

There is no importance in the order of mixing of the water, the guanidine salt, the ion-exchange resin, and any conventional additives in the system. Normally, however, it is simplest to prepare an aqueous solution of the guanidine salt, with the other additives contained therein, and then add that solution to the ion-exchange resin. The guanidine salt will preferably be in the form of an aqueous solution having at most about 40% by weight of the guanidine salt, preferably less than 35% by weight of the guanidine salt, and generally having at least about 1.2% by weight of the guanidine salt. An increase or decrease in the concentration of one component of the system may be compensated by an appropriate adjustment to the concentration of the other ingredient, and to the ratio of the two ingredients in the system. The important item, however, is the concentration of the resulting guanidine hydroxide in the guanidine hydroxide solution, and that concentration should be within the ranges set forth above. As applied to the hair, the relaxer composition of the present invention will not contain any sulfur-based keratin-breaking agents, and preferably the active components of the system do not contain, as applied to the hair, any organic sulfurcontaining compounds. Thiourea may be utilized as an accelerator, but this is normally unnecessary and is not preferred. Sulfur-containing compounds may be in the initial mixture of guanidine salt and ionexchange resin, such as, for instance, guanidine sulfate or guanidine sulfite or their bisulfate and bisulfite analogues. These compounds, however, would not be active ingredients in treating hair per se, and the sulfate and/or sulfite ions would be bound to the ion-exchange resin, to the extent of the resin exchange capacity, and in that form would certainly not be an active agent in the hair treatment. Thus, the system and method of the present invention can be readily distinguished from prior art compositions and methods based upon thioglycolates or sulfites as active ingredients.

The guanidine hydroxide aqueous solution-based system which is applied to the hair according to the method of the present invention should have a relatively high pH. The pH value of the guanidine hydroxide solution is generally above 11.8, preferably about 12.5 to about 13.5, and most preferably around 13.0.

Normally an excess of the ion-exchange resin will be utilized, as an excess of the guanidine salt will frequently reduce the pH of the resulting mixture, to the point that the guanidine hydroxide may not act efficiently to treat hair. For the most efficient ion exchange systems, the mole ratio would theoretically be 1:1, but this condition is difficult to achieve, and normally the ion exchange ratio will be within the range of 1:2–1:3 of guanidine salt:ion-exchange resin. The ratio may be as high as 1:7.5, or even as high as 1:10, but for commercial embodiments it is anticipated that the ratio will be within the aforesaid preferred range.

Conventional additives may be present in the systems of the present invention in order to provide their known functions therein. For instance, the guanidine salt may be in an aqueous cream component, which can contain an emulsifier, a thickener, an emollient, and/or a humectant. Preservatives may be added to the system, and accelerators may also be present, especially if low concentrations of guanidine hydroxide are utilized.

Thorough mixing of the ingredients of the system, especially when a cream or emulsion is utilized, is strongly recommended. The ion exchange reaction between the ion-exchange resin and the guanidine salt generally proceeds relatively rapidly upon adequate mixing, and normally is substantially complete within a few minutes time. For some systems, the ion exchange reaction will be substantially complete within one minute or so, and in the preferred system the ion exchange reaction will be completed within two minutes or so. For some systems, however, additional time for the ion exchange reaction to proceed must be allowed, and times as long as five or even ten minutes may be indicated for particular systems of particular ion-exchange resins and guanidine salts. A rough indication of the amount of time required can be obtained by measuring the time for a given mix system to reach an equilibrium pH. Such an equilibrium pH is achieved when the pH of the mixed system remains substantially constant for several minutes. The time at which such pH is first reached can be readily determined, by use of a monitoring pH probe, and the time at which such pH is first achieved can be considered the equilibrium pH time.

It is preferred to utilize a system which achieves an equilibrium pH within 1–2 minutes of mixing, to insure that the ion exchange reaction is substantially complete. However, the presence of the ion-exchange resin on the hair upon application of the system permits the ion exchange reaction to continue on the hair itself, so that the system can be applied to the hair before the ion exchange reaction is substantially complete.

While creams or emulsions may be used in some instances, for certain guanidine salts, such as guanidine alginate, the salt itself may have sufficient thickening ability that other thickeners or emulsifiers are unnecessary.

The use of guanidine hydroxide as a hair treating agent, for straightening or relaxing hair, or for curling hair, is disclosed in the co-pending application of Mario de la Guardia, Ser. No. 805,149, which is hereby incorporated by reference for such teachings.

The time of treatment of hair which is to be treated according to the present invention, with the system of the present invention, will normally be within the range of 5 to 45 minutes, with the time starting from the first application of the system to the hair. Normally this treatment time will be at least 10 minutes, and there is no real upper limit on the time that the system can remain on the hair, with the above-noted 45 minute time generally being about the greatest length of time that is acceptable to end users. It is greatly preferred to utilize a treatment time of no more than about 30 minutes, and preferably less than about 25 minutes. Most preferably the treatment time will be in the neighborhood of about 20 minutes or so.

After the above treatment time has elapsed, the remaining system should be removed from the hair in order to prevent further decrease of the strength retention of the treated hair. A major portion of the guanidine hydroxide and of the ion-exchange resin can be removed from the hair by thorough rinsing. The rinsing step may be preceded by a combing step, if relatively large particle size ion-exchange resins are utilized. It is preferred that the rinsing step be followed by a neutralizing step, using any suitable neutralizing agent. A buffered neutralizing shampoo has been found to be effective, but any conventional neutralizing methods and compositions, well known to the art, may be utilized. For instance, critic acid may be added to a conventional shampoo until the pH of the acidified shampoo has been reduced to 5.0 or so to form an effective neutralizing shampoo. Preferably the hair is neutralized by reducing the pH thereof to a value of no greater than about 7, and more preferably to a value of about 5.0–6.5. While lower pH values may be used, it is generally preferred to maintain the pH of the treated hair within the range of about 5.0 to about 7.0.

Generally the composition will be applied to the hair at ambient temperature, but the composition may be at a temperature of say 35°–140° F. if desired. No advantages will be obtained by working outside of this temperature range.

The commercial hair curling compositions now on the U.S. market appear to be based on ammonium thioglycolate or sodium sulfite and/or ammonium sulfite. These compositions produce a decidedly unpleasant odor of mercaptans, ammonia and/or sulfur dioxide. In addition to the advantages described hereinabove, another decided advantage of the system of the present invention, when used for curling applications, is freedom from such objectionable odors.

EXAMPLES OF THE INVENTION

Example 1

Duolite A 104, a benzyltrimethylammonium chloride ion-exchange resin manufactured by Diamond Shamrock, having a rated salt splitting capacity of 3.5 meq/g was placed in a 1 liter beaker having a magnetic stirrer. The approximately 600 grams of resin were washed with 1 N hydrochloric acid, filtered, rinsed several times with deionized water and then washed with a 1 N sodium hydroxide solution to convert the chloride ions on the resin to hydroxide ions. The beaker was decanted and the degree of conversion checked by adding silver nitrate to the decantate (a precipitate indicates that chloride ions are still being removed from the resin). After the ion exchange reaction was complete, the beaker was decanted and the resin contained therein washed with deionized water.

A guanidine hydrochloride solution having a pH of approximately 7 was formed by dissolving 23.21 grams of guanidine hydrochloride in 500 ml of deionized water. About 300 ml of the ion-exchange resin prepared above, having an apparent density of 720–750 g per liter, was placed in a beaker and covered with the guanidine hydrochloride solution. After stirring 30 minutes at room temperature (to ensure complete ion exchange), a decantate portion of the beaker was checked for the presence of chloride ions, and no such ions were present.

Ten weight percent of cetomacrogol wax emulsifier, and 2.5 weight percent of cetyl alcohol thickener were added to the beaker contents, and then the beaker contents were applied to medium-to-fine texture brown virgin hairs. Ten hairs were wound on a 5 mm diameter glass rod and retained on tne rod with tape and rubber bands. The beaker contents were applied to the wound hairs by a spatula. The formulation was allowed to contact the hairs for 15 minutes and then the formulation was rinsed from the hairs using warm tap water for 2 minutes. The treated hairs were neutralized to a pH of 6.4–6.5, again rinsed in warm tap water and blow dried for 5 minutes with a hair dryer. The hairs were removed from the glass rod by cutting in order to avoid any straightening of the curls, and allowed to remain at ambient conditions for 18 hours, after which the curls were measured for curl diameter and hair length. The treated hairs had a smaller curl diameter and a shorter hair length than the control, which were hairs treated with thickened deionized water.

Example 2

Guanidine hydroxide was prepared following the general procedure of Example 1, with all steps conducted under a nitrogen blanket to exclude carbon dioxide. A solution containing 5 percent by weight of guanidine hydroxide was obtained in the beaker. Titration of the beaker's contents indicated that no carbonate was present.

About 25–35 medium texture, kinky Negro hairs were clamped in a straightened position on a glass rod and then immersed into the room temperature beaker contents, containing the guanidine hydroxide solution and the ion-exchange resin therein. Two tests were conducted, at 20 and 30 minutes immersion time. The guanidine hydroxide and the ion-exchange resin were rinsed from the hairs using warm tap water for 2 minutes, and then the rinsed hairs were neutralized to a pH of 6.4–6.5, rinsed again and blow dried. Upon removal of the clamps, a noticeable increase was observed in the straightening effect which was obtained in each test, as compared to a control test wherein the hairs were immersed in deionized water.

Examples 3-15

These examples relate to the production of guanidine hydroxide by ion exchange with a number of different guanidine salts. The ion-exchange resin utilized in these examples was Duolite A-104, having a rated exchange capacity of 3.5 meq/g, and an actual, measured exchange capacity of 3.1 meq/g. The Duolite A 104 had a particle size of 16-50 mesh. In these examples, the guanidine salts listed were utilized in an amount corresponding to 0.00348 moles of guanidine. The appropriate amount of guanidine salt was dissolved in 10 ml of water (with the exception of the guanidine laurate, wherein 15 ml of water was used) and then the resulting guanidine salt solution was added to the Duolite A 104 resin, with the resin also having 10 ml of water added thereto prior to the guanidine salt solution addition. The amount of resin was that required to produce the indicated mol equivalent ratios. Before the guanidine salt solutions were added to the resin, they were titrated to a pH of 8, so tht equal starting pHs were utilized. The resins were titrated with either guanidine hydroxide, when their pH was less than 8, or with an acid corresponding to the guanidine salt anion, when the pH was greater than 8. In every instance except for the use of guanidine alginate (which produced a gel), the resin/guanidine salt mixture was stirred.

The table set forth below gives the results of making guanidine hydroxide systems according to these examples.

| Example | Guanidine Salt | Mole Equivalent Ratio, Salt:Resin | Final Measured pH | Time to Reach pH equilibrium, minutes |
|---|---|---|---|---|
| 3 | Sulfate | 1:6.6 | 13.50 | 2 |
| 4 | Carbonate | 1:5.6 | 12.95 | 2 |
| 5 | Hydrochloride | 1:7.7 | 13.30 | 1 |
| 6 | Nitrate | 1:6.6 | 13.30 | 2 |
| 7 | Tartrate | 1:6.3 | 13.30 | 1 |
| 8 | Sulfite | 1:6.5 | 13.25 | 1 |
| 9 | Laurate | 1:6.6 | 12.80 | 8 |
| 10 | Phosphate | 1:7.6 | 13.10 | 3 |
| 11 | Fluoride | 1:7.5 | 12.95 | 2 |
| 12 | Oxalate | 1:6.5 | 13.30 | 1 |
| 13 | Thioglycolate | 1:7.2 | 12.95 | 5 |
| 14 | Acetate | 1:7.2 | 12.85 | 2 |
| 15 | Alginate | 1:6.8 | 12.58 | 2 |

All of the ion exchange products produced by the above ion exchange reaction would effectively straighten or relax kinky Negro hairs, following the procedures of Example 2.

In the above Examples, the system of the present invention was applied to hair by immersing the hair in the system. In normal consumer application, however, the system of the present invention will be applied to the hair by various means, depending, e.g., upon the viscosity of the system. The system may be applied with a spatula, poured over curlers, sponged onto the hair, etc.

The method and system of the present invention can be used to curl hair, but the results obtained to date suggest that the most advantageous application for the present invention is to straighten, or relax, kinky hairs of the Negroid type.

What is claimed is:

1. A method of treating hair to cause the hair to maintain a desired configuration, said method comprising contacting the hair while in said desired configuration with an effective amount of an aqueous composition comprising the product formed by mixing in an aqueous medium at least one water-soluble quanidine salt in solution in said aqueous medium in an amount of greater than 0.25 molar in quanidine and an effective amount of at least one particulate, strong-base, quaternary ammonium, hydroxide-form ion-exchange resin, wherein said resin has an affinity for the anion of said quanidine salt which is at least equal to the affinity of the resin for the hydroxyl ion, and removing said composition from the hair after said composition has been in contact with the hair for an effective time.

2. Method of claim 1, wherein said ion-exchange resin is in finely divided form.

3. Method of claim 1, wherein said salt is selected from the group consisting of guanidine sulfate, guanidine hydrochloride, guanidine nitrate, guanidine tartrate, guanidine sulfite and guanidine oxolate.

4. Method of claim 1, wherein said guanidine salt and said ion-exchange resin are mixed together at a temperature of about 5° to about 95° C.

5. Method of claim 1, wherein said desired configuration is a straightened configuration, and the hair is in the straightened configuration at least during a portion of the time it is contacted by said aqueous composition.

6. Method of claim 1, wherein said guanidine salt is selected from the group consisting of guanidine sulfate, carbonate, hydrochloride, nitrate, sulfite, phosphate, fluoride, oxalate, thioglycolate and alginate and guanidine carboxylic acid salts of alkane and alkene carboxylic acids having from 2 to about 20 carbon atoms.

7. Method of claim 2, wherein the resin has a particle size of less than 400 mesh.

8. A system for treating hair to cause the hair to maintain a desired configuration, said system comprising an aqueous medium containing a hair treating-effective amount of guanidine hydroxide and at least one particulate, strong-base, quaternary ammonium ion-exchange resin having bound thereto at least a stoichiometric amount, based on the amount of said guanidine hydroxide, of an anion which when combined with the guanidine ion produces a water-soluble salt, said resin having an affinity for said anion at least as great as for the hydroxyl ion.

9. System of claim 8, wherein said system is suitable for straightening hair to cause the hair to maintain a straightened configuration.

10. System of claim 8, wherein said resin has a particle size of less than 400 mesh.

11. System of claim 8, wherein said anion is selected from the group consisting of sulfate, nitrate, tartrate, oxolate, hydrochloride and sulfite anions.

12. A method of treating hair to cause the hair to maintain a desired configuration, said method comprising contacting the hair while in said desired configuration with an effective amount of an aqueous composition comprising the product formed by mixing in an aqueous medium at least one water-soluble guanidine salt in solution in said aqueous medium in an amount of greater than 0.25 molar in guanidine and an effective amount of at least one particulate, strongbase, quaternary ammonium, hydroxide-form ion-exchange resin, wherein said resin has a salt splitting capacity of at least about 3.0 meq/g. and an affinity for the anion of said guanidine salt which is at least equal to the affinity of the resin for the hydroxyl ion, and removing said composition from the hair after said composition has been in contact with the hair for an effective time.

13. Method of claim 12, wherein said salt splitting capacity is at least about 3.5 meq/g.

14. Method of claim 13, wherein at least 40 grams of resin are used to treat each adult head of hair.

15. Method of claim 14, wherein at least 50 grams of said resin are used for each adult head of hair.

* * * * *